(12) United States Patent
De Oliveria Garcia Da Fonseca

(10) Patent No.: US 9,594,016 B2
(45) Date of Patent: Mar. 14, 2017

(54) PHOTOMETRIC DEVICE AND METHOD

(71) Applicant: BIOSURFIT, S.A., Aveiro (PT)

(72) Inventor: Joao Manuel De Oliveria Garcia Da Fonseca, Azambuja (PT)

(73) Assignee: Biosurfit, S.A., Aveiro (PT)

( * ) Notice: Subject to any disclaimer, the term of this patent is extended or adjusted under 35 U.S.C. 154(b) by 153 days.

(21) Appl. No.: 14/361,620

(22) PCT Filed: Nov. 29, 2012

(86) PCT No.: PCT/EP2012/074005
§ 371 (c)(1),
(2) Date: May 29, 2014

(87) PCT Pub. No.: WO2013/079619
PCT Pub. Date: Jun. 6, 2013

(65) Prior Publication Data
US 2015/0085275 A1   Mar. 26, 2015

(30) Foreign Application Priority Data

Dec. 1, 2011 (PT) .......................... 106036

(51) Int. Cl.
*G01N 33/48* (2006.01)
*G01N 21/47* (2006.01)
(Continued)

(52) U.S. Cl.
CPC ........ *G01N 21/4738* (2013.01); *G01J 1/0223* (2013.01); *G01N 21/031* (2013.01);
(Continued)

(58) Field of Classification Search
CPC .................................................... G01N 33/48
(Continued)

(56) References Cited

U.S. PATENT DOCUMENTS 5,310,222 A * 5/1994 Chatwin ................ G03H 1/02
283/109
5,986,754 A * 11/1999 Harding ................ G01N 21/05
356/246

(Continued)

FOREIGN PATENT DOCUMENTS

EP 0 704 691 A2 4/1996
EP 1 752 758 A1 2/2007
(Continued)

OTHER PUBLICATIONS

"Direct hemoglobin measurement by monolithically integrated optical beam guidance", M. Grumann et al. Transducers'05, pp. 1106-1109 (2005).

(Continued)

*Primary Examiner* — Roy M Punnoose
(74) *Attorney, Agent, or Firm* — Patterson Thuente Pedersen, P.A.

(57) ABSTRACT

Disclosed are methods and devices for photometric measurements of a liquid sample. The methods and devices use one or more diffractive reflective surfaces to enable a light beam incident on a measurement chamber to be steered so as to be reflected inside the measurement chamber to achieve relatively long optical paths in the measurement chamber. The liquid sample may be blood or blood serum. The measurement chamber may be provided in a microfluidic device, for example a centrifugal microfluidic device. Some embodiments enable multiplexing of different wavelengths or path lengths. Some embodiments make use of multiple returned beams to determine the position and/or orientation of the measurement chamber.

19 Claims, 11 Drawing Sheets

(51) Int. Cl.
    *G01N 21/03*     (2006.01)
    *G01N 21/07*     (2006.01)
    *G01J 1/02*     (2006.01)
    *G01N 33/92*     (2006.01)

(52) U.S. Cl.
    CPC ......... *G01N 21/0303* (2013.01); *G01N 21/07* (2013.01); *G01N 33/92* (2013.01); *G01N 2021/0325* (2013.01); *G01N 2201/062* (2013.01); *G01N 2201/0612* (2013.01); *Y10T 29/49826* (2015.01)

(58) Field of Classification Search
    USPC .......................................................... 356/39
    See application file for complete search history.

(56) References Cited

U.S. PATENT DOCUMENTS 6,632,399 B1 * 10/2003 Kellogg .............. B01F 13/0059
                                                    422/505

8,834,004 B2 * 9/2014 Thompson ........... G02B 6/0035
                                                    362/617
2013/0114076 A1 * 5/2013 Schleipen ............ A61B 5/0059
                                                    356/246

FOREIGN PATENT DOCUMENTS

| JP | H08114501 A | 5/1996 |
| JP | 2009270964 A | 11/2009 |
| WO | WO 2010/077159 A1 | 7/2010 |
| WO | WO 2011/125440 A1 | 10/2011 |

OTHER PUBLICATIONS

Office Action dated Jul. 19, 2016 for Japanese Application No. 2014-543898, 3 pages.

* cited by examiner

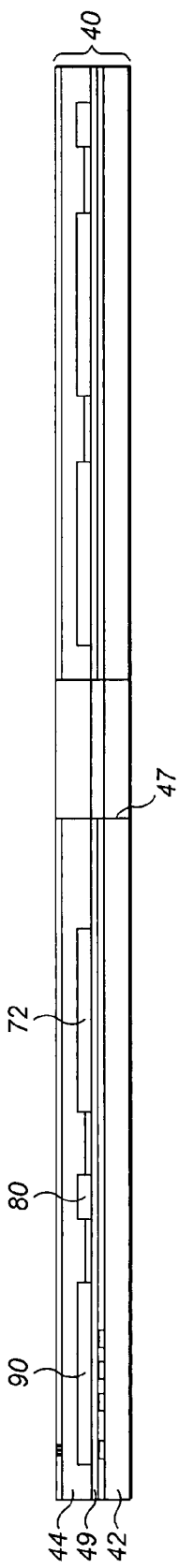

PHOTOMETRIC DEVICE AND METHOD

PRIORITY CLAIM

This application is a National Phase entry of PCT Application No. PCT/EP2012/074005, filed Nov. 29, 2012, which claims priority from Portugal Application No. 106036, filed Dec. 1, 2011, the disclosures of which are hereby incorporated by referenced herein in their entirety.

FIELD OF THE INVENTION

The present invention relates to a photometric measurement method and system, as well as to sample chambers for such a method and system, in particular although not exclusively for the analysis of blood or blood plasma samples.

BACKGROUND OF THE INVENTION

Photometric measurements are used for a variety of applications. For example, materials or systems to be measured may affect light differentially as a function of light wavelength. One major application concerns the determination of the presence and quantification of compounds in a certain liquid. In particular, in the biological and medical fields, this usually requires the measurement of light intensity after passing along an optical path through a liquid, such as blood serum, containing compounds to be determined. For most such applications, in particular those exploiting multiplexed measurements of limited sample volumes and miniaturization, there is a significant limitation on available liquid volume and hence the length of the optical path.

The above applications are based on light absorption in the liquid, and therefore signal to noise ratios are directly proportional to the optical path length.

Many applications exploit planar configurations with microfluidic setups, having large in-plane areas and small in-depth profiles. Previous work used micro-prisms and liquid routing to increase optical paths without sample volume increase. See for example. "Direct hemoglobin measurement by monolithically integrated optical beam guidance", M. Grumann et al. TRANSDUCERS'05 pi 106-1109 (2005), incorporated herein by reference. Such devices have significant disadvantages related to manufacturability and usability.

Therefore there is a significant need for enhanced devices and methods capable of high precision photometric measurements in small liquid volumes, in particular highly multiplexed measurements, and yet being simple to manufacture and operate.

SUMMARY OF THE INVENTION

In a first aspect, there is disclosed a method of deriving a photometric measure.

Advantageously, by using reflected diffraction orders of incident light, light can be controllably steered to be reflected (by total internal reflection or otherwise) one or more times in a sample chamber and then made to exit the sample chamber by a further diffraction. This allows the path length inside the sample to be increased and controlled.

In some, wavelength multiplexed embodiments, a first diffraction can be used to align and steer together beams of different wavelength, which will then separate again on further diffractions. In yet some further embodiments, by interspersing non-diffracting surfaces between a plurality of diffractive surfaces, propagation in the sample by substantially lossless reflection can be combined with the ability to cause the beam travelling in the sample to exit the sample by a final diffraction. This enables greater intensity to be maintained for the beam exiting the sample as compared to embodiments in which each reflection is associated with a corresponding diffraction. These embodiments can be combined with the wavelength multiplexed embodiments to increase signal intensity achievable in these embodiments for a given optical path length.

In a second aspect, there is disclosed a photometric measuring chamber.

By providing a measuring chamber with a reagent for photometric measurements and a reflective diffractive surface, when used in a system as described above, the above method is enabled. The photometric measuring chamber can be used in conjunction with blood or blood serum samples by choice of reagents or any other liquid in which light absorption is affected by the interaction between molecules in the liquid and the reagent. Further, by using diffraction to steer a light beam, devices incorporating the measurement chamber may be manufactured using efficient mass production techniques, for example involving standard CD/DVD manufacturing processes.

In a third aspect, there is disclosed a photometric measuring chamber.

When used in the way described above, an increased intensity signal for a given optical path length is enabled.

In a fourth aspect, there is provided a method of making a cartridge having a plurality of sample chambers.

Advantageously, by selective placement of apertures in an opaque layer applied to a clear disc part defining the chambers, different optical path length can achieved in the sample chambers with low manufacturing overheads. This is most advantageous when multiple distinct diffractive surfaces are present, but is also applicable more widely.

In overview, the disclosure provides new photometric devices and operation methods using reflective gratings inside microfluidic chambers. Further disclosed are enhanced devices and operation methods for multiple wavelength adsorption and photometric measurements in static and moving sample cartridges.

One embodiment relates to incidence of light into a sample liquid with a certain wavelength and, in sequence: (i) diffraction in a first reflective diffractive grating; (ii) total internal reflection in or at a surface confining the liquid sample; (iii) at least one second diffraction that enables the light to exit the sample holder; (iv) optical measurement components to measure the light existing the sample. Exploiting multiple diffractions of, for example, opposite signs (e.g. +1 then −1 diffraction orders) spaced in between at least one total internal reflection enables the measurement of light properties with a relatively long optical path for small liquid sample volumes.

One further embodiment relates to multiple wavelength beams travelling in a sequence of: (i) diffraction in a first reflective diffractive grating; (ii) total internal reflection in or at a surface confining the liquid sample; (iii) at least one second diffraction that enables the light to exit the sample holder; (iv) optical measurement components to measure the light existing the sample. A device may be built in this embodiment with reduced manufacturability limitations and may be easily operated in order to obtain high-resolution photometric measurements in very small liquid sample volumes.

Another embodiment relates to the measurement of multiple diffracted orders of different wavelengths, each travelling in a liquid sample volume with a first diffraction and at least one total internal reflection. Devices using the disclosed principles may be built without undue manufacturability limitations and may be easily operated in order to obtain not only high-resolution photometric measurements in very small liquid sample volumes but also self-referencing measurements for either internal quality control purposes or for multiplexing compound quantification.

One additional embodiment relates to devices according to the previous descriptions and further including light slits in the sample cartridge, enabling the use of the device for different light paths without significant light intensity loss. Furthermore, a high-multiplexed cartridge may be manufactured using essentially identical liquid detection zones. By only changing one of the final manufacturing process steps consisting of opening optical slits at predefined positions, one may then have different optical paths for different photometric measurements for different compound quantifications.

One further embodiment relates to movable cartridges, namely rotating cartridges, capable of performing complete multiplexed photometric measurements from a given fluid, for example blood. A device integrating different structures and units and operated in a predefined manner may provide a total analytical system with significant advantages when compared to traditional analytical devices.

One further embodiment relates to multi-parameter blood analysis using the enhanced photometric configuration disclosed. One yet further embodiment relates to the enhanced operation of a device having a grating and enabling the measurement of multiplexed photometric properties. Furthermore, the operation of the disclosed device can use self-referencing and internal quality control measurements in movable cartridges for analytical purposes.

BRIEF DESCRIPTION OF THE DRAWINGS

Specific embodiments are now described by way of example only to illustrate the principles of the present disclosure and with reference to the accompanying drawings, in which:

FIG. 7A illustrates a transverse section of the centrifugal cartridge illustrated in FIG. 6;

DETAILED DESCRIPTION OF THE DRAWINGS

Figure 1:
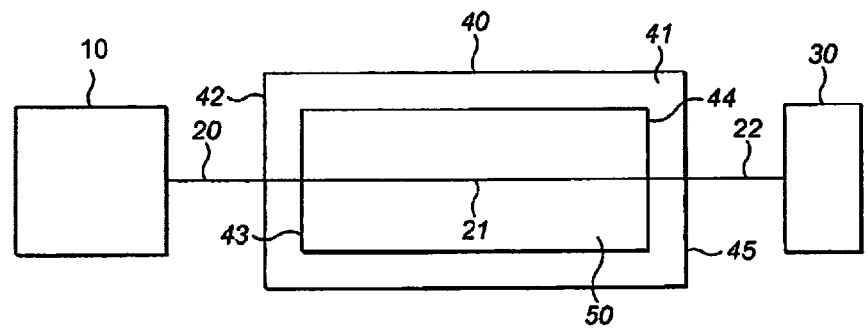
FIG. 1 illustrates a conventional photometric measurement device.

FIG. 1 illustrates a known conventional photometric measurement device. A prior art emitter (10) emits light (20) with multiple wavelengths into a detector (30) passing through a liquid container (40) containing liquid (50) with properties to be characterized. The container (40) is made in such a way that its surfaces (41) to (44) do not have significant light absorption coefficients. The liquid volume is typically at least several micro-liters and the liquid container of dimensions of at least several millimeters.

Figure 2:
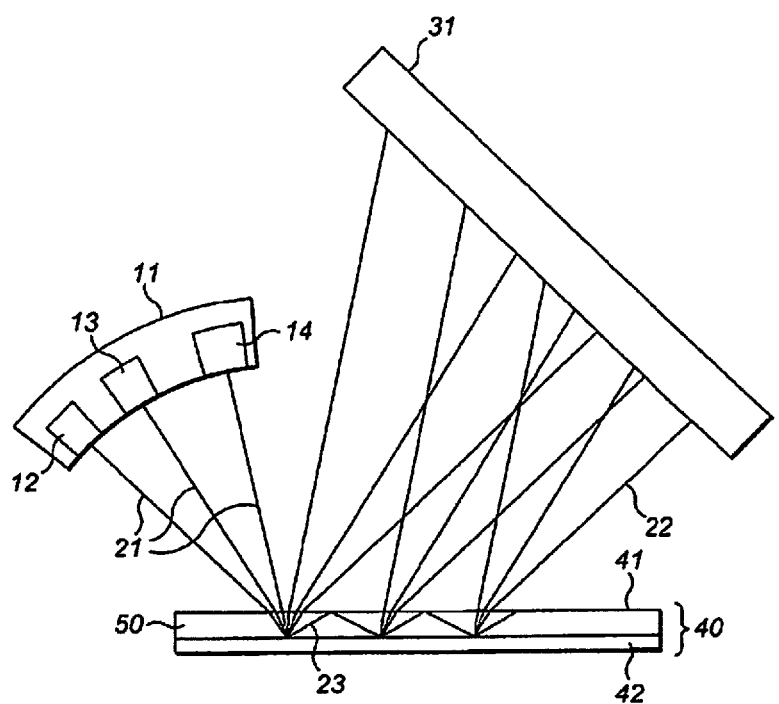
FIG. 2 illustrates a photometric measurement device according with a diffraction grating.

FIG. 2 illustrates a photometric measurement device embodying disclosed principles. An emitter (10) contains components emitting beams of specific wavelengths (12), (13) and (14). Each component is placed at a specific orientation with respect to a cartridge (or other sample chamber) (40), so that light passes through the liquid (50) onto a reflective diffractive layer (42). The diffractive order +1 of each beam is substantially at the same angle inside the cartridge, and is sufficiently tangential to the upper surface (41) of the cartridge (40) so to result in total internal reflection inside the liquid (50). Light of each beam is then diffracted at least once again. The diffracted order −1 is sufficiently perpendicular to the upper surface (41) of the cartridge (40) to escape the cartridge. A detector (31) is used to measure the light intensity of the beams of different wavelengths, different optical path lengths and, in some embodiments, of different diffractive orders.

The emitter module (11) may contain several discrete elements (12), (13), etc arranged in such a way to obtain essentially the same angle of first reflective diffraction order inside the liquid (23).

Figure 3:
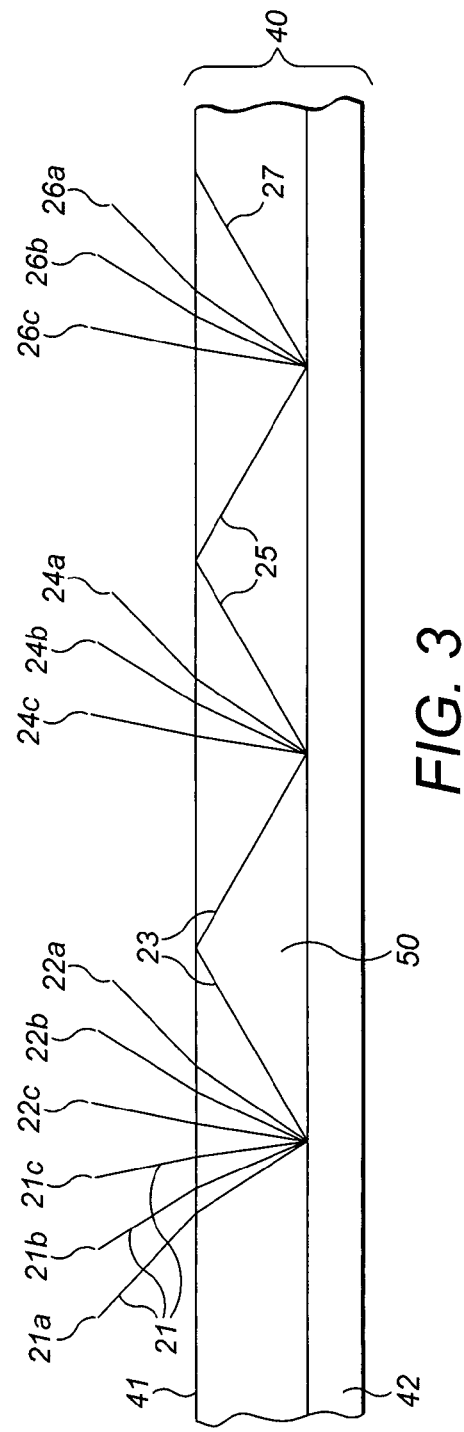
FIG. 3 illustrates details of the device of FIG. 2.

FIG. 3 provides further details of the illustration of FIG. 2. The incident beams of different wavelengths (21) have different incident angles arranged in such a way that the first order diffraction (23) is oriented with respect to the surfaces (41) and (42) in essentially the same way for all beams. The zero-order diffraction (22) (i.e. light beams) exit the cartridge (40) and may be used in measurements. After the fist total internal reflection, a second diffraction occurs. In this case, the zero order diffraction (25) follows the same orientation and again is totally internal reflected in the upper surface (41) of the cartridge (40) (or at the liquid/cartridge interface). The −1 order diffraction (24) exits the cartridge in different angles depending on the wavelength (24a), (24b) and (24c). The process may be repeated again with a third diffraction on the grating surface (42), with additional −1 order diffraction beams (26) exiting the cartridge.

In one embodiment, the emitter (11) contains 2 collimated LEDs with wavelengths of 340 nm and 405 nm, with TE polarization, placed with fixed orientation with respect to the cartridge at angles 46.6° (340 nm) and 40.2° (405 nm), Both LEDs are directed to essentially the same point at the lower surface (42) of the cartridge (40). A diluted blood plasma solution (50) is inserted in the cartridge (40), with a dilution of 1:21 with PBS, having a refractive index n_liq=1.33. The cartridge detection zone has a liquid thickness of 0.2 mm. The 340 nm beam is incident at the diffraction surface (43) with an angle of 33.1° and the 405 nm beam is incident ate the diffraction surface (43) with an angle of 29.0°. The diffraction surface consists of a sine-trapezoidal grating of 800 nm period, 50 nm height of polycarbonate covered by 100 nm of gold. The zero order of both beams exits the cartridge and both are incident to the detector (31), with overall efficiencies of 23.6% (340 nm) and 27.4% (405 nm). Both beams are diffracted with a first reflective diffractive order at 60° from the diffractive surface, with overall efficiencies of 3.8% (340 nm) and 3.0% (405 nm). These diffracted beams are totally internally reflected from the upper surface of the cartridge (40) since the incidence angle at the cartridge-air interface is beyond the totally internal reflection angle (for n_liq=1.33, theta tir ~48.7°). This first total internal reflection occurs at a distance of ~0.4 mm from the initial diffraction spot. At a distance of ~0.8 mm from the initial diffraction spot, a second diffraction occurs, with the zero order following the same 60° angle, and the minus one order having an incidence angle of 33.1° (340 nm) and 29.0° (405) with overall efficiencies of 0.23% (340 nm) and 0.14% (405 nm). The zero order of the second diffraction has overall efficiencies of 1.8% (340 nm) and 1.6% (405 nm) and is again totally internal reflected at the upper surface (42) of the cartridge. At a distance of ~1.6 mm of the initial diffraction spot, a third diffraction occurs, with its minus one orders having overall efficiencies of 0.11% (340 nm) and 0.07% (405 nm) exiting the cartridge and being measured at the detector. Again, a zero order is propagated along the liquid (50).

The total path length in the liquid and for each wavelength is ~0.5 mm (first beam with zero diffraction), ~1.3 mm (second beam, −1 diffraction of +1 diffraction after 1 totally internal reflection) and ~2.1 mm (third beam −1 diffraction of +1 diffraction after 2 totally internal reflections). There are small differences of the total path length in the liquid for each wavelength (~4% for the first beam, ~2% for the second beam and ~1% for the third beam). Other diffraction orders occur in each diffraction, and in some cases these may have significant intensities that need to be also considered. In the example here detailed, a 2 reflective diffraction beam occurs at angles of −13.1° (340 nm) and ~6° (405 nm), but these beams have intensities at least one order of magnitude lower than the −1 diffractive orders and therefore do not interfere in the relevant signal acquisitions.

The above example illustrates the possible use for photometric applications of consecutive diffractions of different beams having discrete different wavelengths and of diffraction orders of opposed signs (e.g. −1 diffraction order of a +1 diffraction order) wherein between there occurs a total internal reflection of a normal transparent surface. The relatively low intensities of the observed beams (e.g. −0.1% of the initial beam intensity) is not a significant limitation in practice, since high initial intensities may be used. The number of consecutive opposed diffractions may also be increase for longer optical path lengths. In the above example, the forth diffraction corresponds to ~2.9 mm of optical path and the fifth diffraction to 18 3.7 mm of optical paths, with beams having intensities of 0.051% and 0.024% respectively (340 nm) and 0.004%> and 0.001% respectively (405 nm).

On the other hand, it may be considered preferable in many applications to have consecutive beams with intensities not too different, so one may simultaneously measure light spots with different optical paths with a single sensor (e.g. a CCD or CMOS 2D image sensor). For this specific purpose, one may use optimized grating shapes, namely gratings with triangular profiles or lazed sinusoidal profiles or other optimized profiles.

Furthermore, the liquid may include reagents that change light properties according to the presence and concentration of specific compounds, and therefore it may be used for quantitative purposes of specific compounds. In a further example of the above mentioned description, the device is used for the quantification of cholesterol in blood samples. The liquid contains cholesterol esterase, cholesterol dehydrogenase and nicotinamide adenine dinucleotide. Cholesterol esterase induces hydrolysis of cholesterol esters present in blood plasma to form cholesterol and fatty acids. In the presence of NAD+ (nicotinamide adenine dinucleotide), cholesterol dehydrogenase converts cholesterol into cholest-4-en-3-one and NADH and NADH may be quantified by measuring light intensities of the 340 nm and 405 nm light beams (see, for example Kayamori, Y, et al. Endpoint colorimetric method for assaying total cholesterol in serum with cholesterol dehydrogenase. Clin Chem 1999; 45: 2158-2163, incorporated by reference herein), and therefore the device may be used to quantify the concentration of cholesterol in blood plasma samples.

In one embodiment, the emitter (11) contains 5 collimated LEDs with wavelengths of 340 nm, 405 nm, 500 nm, 550 nm and 600 nm, placed with fixed orientation with respect to the cartridge at angles 46.6° (340 nm), 40.2° (405 nm), 31.7° (500 nm), 27.6° (550 nm) and 23.7° (600 nm), all focused at substantially the same point at the lower surface (42) of the cartridge (40). The use of multiple wavelengths such as described may enable the operation of the device for the detection of a wide variety of biological compounds, based on the differential light adsorption following some chemical or enzymatic or other reaction. Many other applications may be seen for photometric systems using the same mechanism, not limited to biological samples nor limited to adsorption measurements.

The above examples may include a significant decrease of light intensity for consecutive diffraction orders, which may be considered too much for some applications or for some devices. Further embodiments provide ways to explore consecutive opposing diffractions occurring between total internal reflections for photometric applications without significant loss of light intensity wherein different lights paths may be used with essentially the same cartridge (40), by a simple change of one element of the cartridge.

Figure 4:
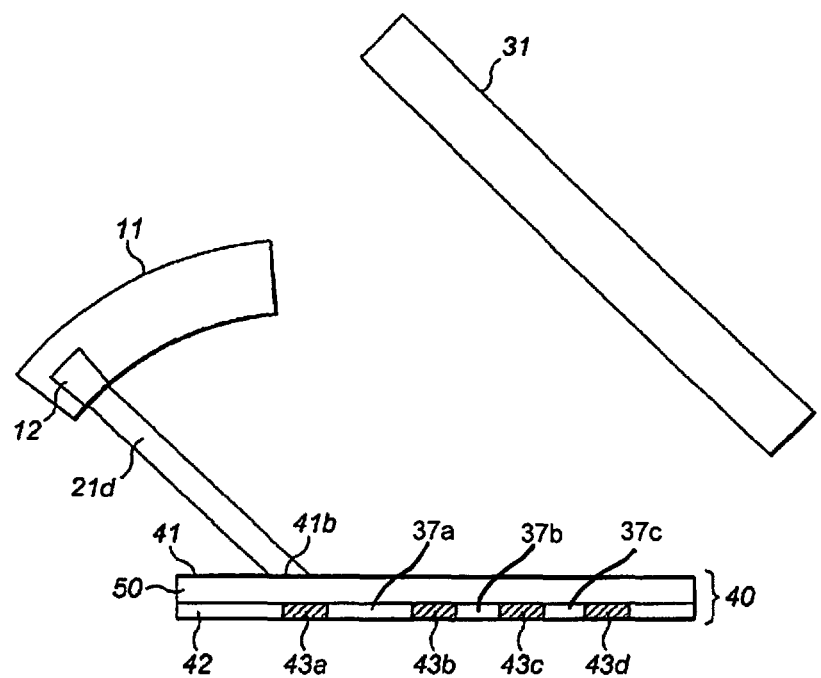
FIG. 4 illustrates a photometric measurement device with tunable optical path length.
Figure 5A:
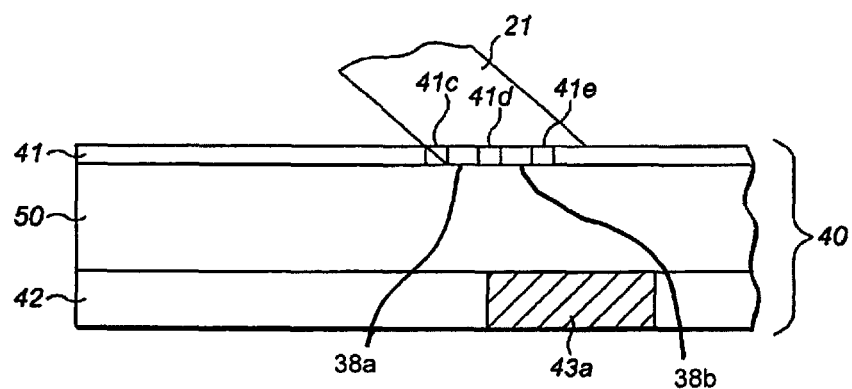
FIGS. 5a-d further illustrates details an entrance region of the device illustrated in FIG. 4.

FIG. 4 illustrates a photometric measurement device according to one embodiment of the present invention, with tunable optical path length. A large collimated beam (21*d*) coming from a light source (12) of an emitter (11) is directed into a cartridge (40) at a particular entrance region (41*b*) of a top cover (41). The device also include a detector (31) and the lower surface (42) of the cartridge (40) contains grating patterns (43*a*), (43*b*), (43*c*) and (43*d*) at different positions that are separated by non-diffractive surfaces (37*a*), (37*b*) and (37*c*). The entrance region (41*b*) of the cartridge 840) has different optical slits or apertures (41*c*), (41*d*) and (41*e*) with an opaque layer (38*a*), (38*b*) located therebetween as shown in FIG. 5*a*. These slits may be either open or closed. The opening or closing of the slits enables the tuning of the optical path length in the liquid (50).

Figure 5B:
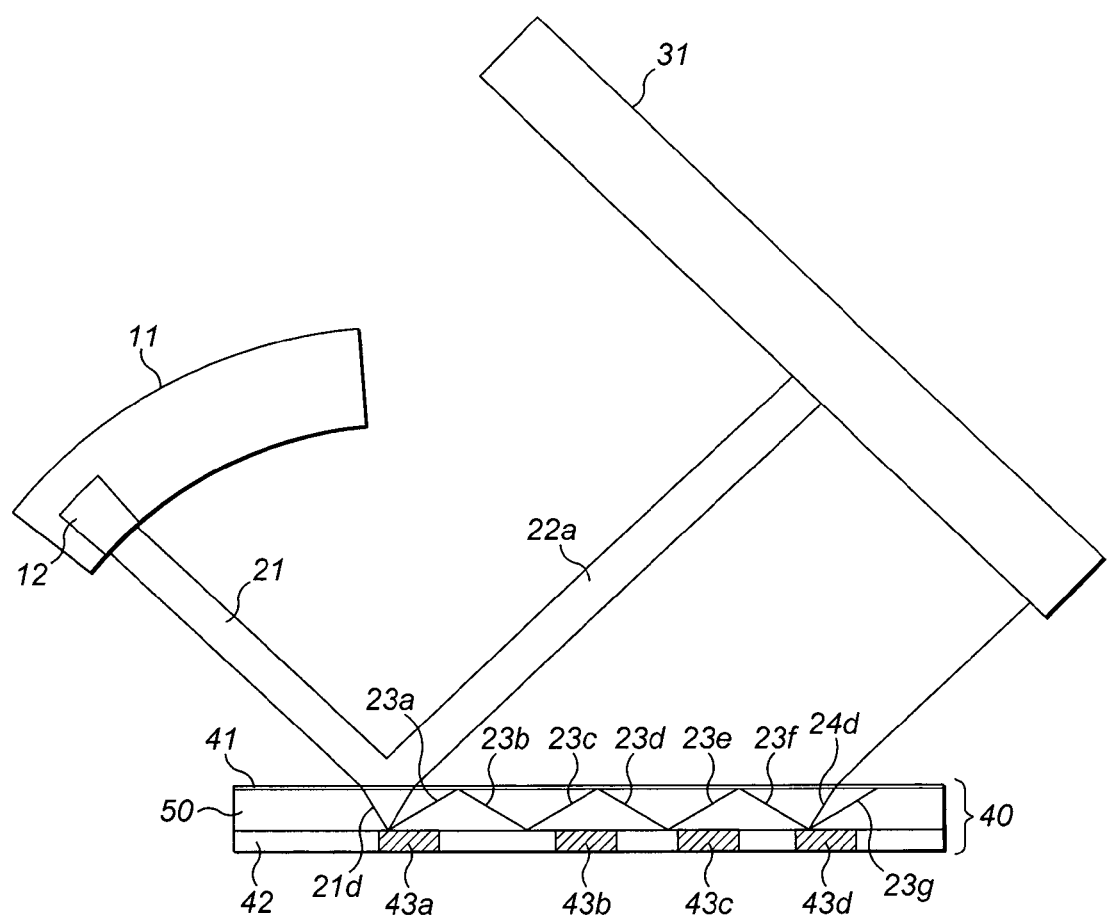

FIG. 5*b* illustrates the case wherein the first slit is opened in the photometric device previously illustrated in FIG. 4. Due to the particular light wavelength, incidence angle and particular position of the grating patterns, a second diffraction occurs only at the last diffraction region (43*d*). From the large incident beam (21) only a narrow beam (21*d*) passes through the liquid (50) and is first diffracted in the first diffraction area (43*a*). The first order diffraction beam (23*a*) is totally internally reflected at the upper surface (41) of the cartridge (40). The positions of the different diffraction patterns (43*a*), (43*b*) (43*c*) and (43*d*) are defined and fixed in such a way that the beam (23*b*) is not incident into the second diffracted pattern (43*b*) but instead is reflected by a flat surface. This surface may either be composed by a reflective layer (e.g. gold) or by a transparent material. In this later case, the beam is again totally reflected since its incident angle is above the totally internal reflection angle. Again, the beam (23*b*) is totally internally reflected in the upper surface (41) and is again incident onto a flat surface, not onto the third diffractive pattern (43*c*). Finally the reflected beam (23*d*) is totally internally reflected and is incident onto the fourth diffractive pattern (43*d*). Here the zero order reflective diffraction beam (23*g*) continues inside the cartridge, but the −1 reflective diffraction order (24*d*) exists the cartridge and is measured in the detector (31). The intensity of the beam (24*d*) may be measured and information may be extracted for quantitative purposes. This configuration may be considered preferable to other configurations since it minimizes optical losses in consecutive diffractions for long optical path lengths. The intensity of the beam (22*a*) may be used for self-referencing. The position of the beam (22*a*) may be used for determining the orientation of the cartridge (40) with respect to the detector and the emitter. The relative position between the beams (22*a*) and (24*d*) may be also used to evaluate the orientation of the cartridge or to directly determine the total optical path inside the liquid (50).

Figure 5C:
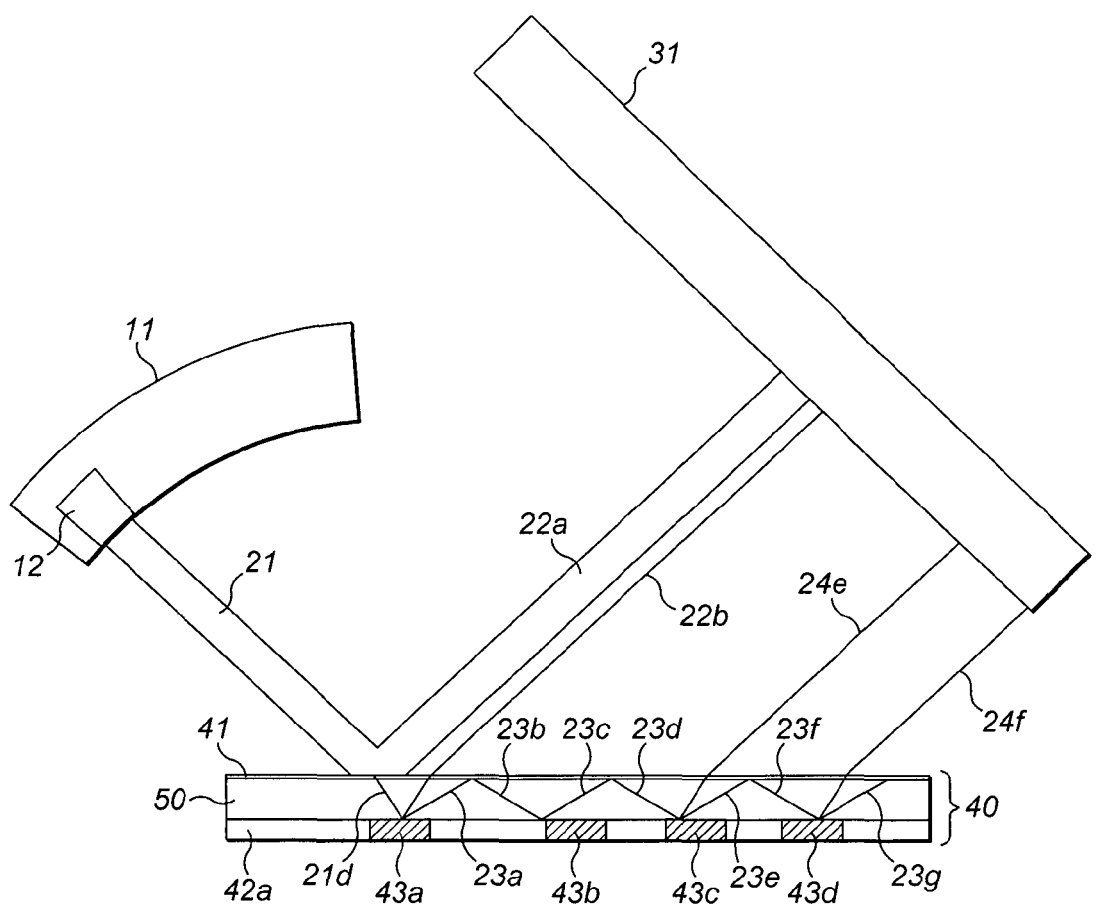

FIG. 5*c* illustrates the case wherein the second slit is opened in the photometric device previously illustrated in FIG. 4. Due to the particular light wavelength, incidence angle and particular position of the grating patterns, a second diffraction occurs at the third (43*c*) diffraction region (and a further diffraction at the fourth diffraction region (43*d*)). From the large incident beam (21) only a narrow beam (21*e*) passes through the liquid (50) and is first diffracted in the first diffraction area (43*a*). The first order diffraction beam (23*a*) is totally internally reflected at the upper surface (41) of the cartridge (40). The positions of the different diffraction patterns (43*a*), (43*b*) (43*c*) and (43*d*) are defined and fixed in such a way that the beam (23*b*) is not incident into the second diffracted pattern (43*b*) but instead is reflected in a flat surface. This surface may either be composed by a reflective layer (e.g. gold) or by a transparent material. In this later case, the beam is again totally reflected since its incident angle is above the totally internal reflection angle. Again, the beam (23*b*) is totally internally reflected in the upper surface (41) and is again incident into a flat surface, not into the third diffractive patter (43*c*). Then the reflected beam (23*d*) is incident to the third diffractive pattern (43*c*). There the zero order reflective diffractive beam (23*e*) is again totally internally reflected in the upper surface (41) and is then incident into the fourth diffractive pattern (43*d*). The minus one reflective diffractive order beam (24*e*) in the surface (43*c*) exits the cartridge (40) and is detected in the detector (31). Furthermore, the minus one reflective diffractive order beam (24*f*) in the surface (43 *d*) also exits the cartridge (40) and is also detected in the detector (31). A device built in such a way may be used for measurement of spectrophotometry properties with increased optical path lengths without significant loss of light intensity up to the third diffraction pattern (43*c*), and therefore, with significant signal to noise ratios. It may also be operated with built-in internal quality controls that are directly related to the intensities and positions of the different light beams (22*b*), (24*e*) and (24*f*).

Figure 5D:
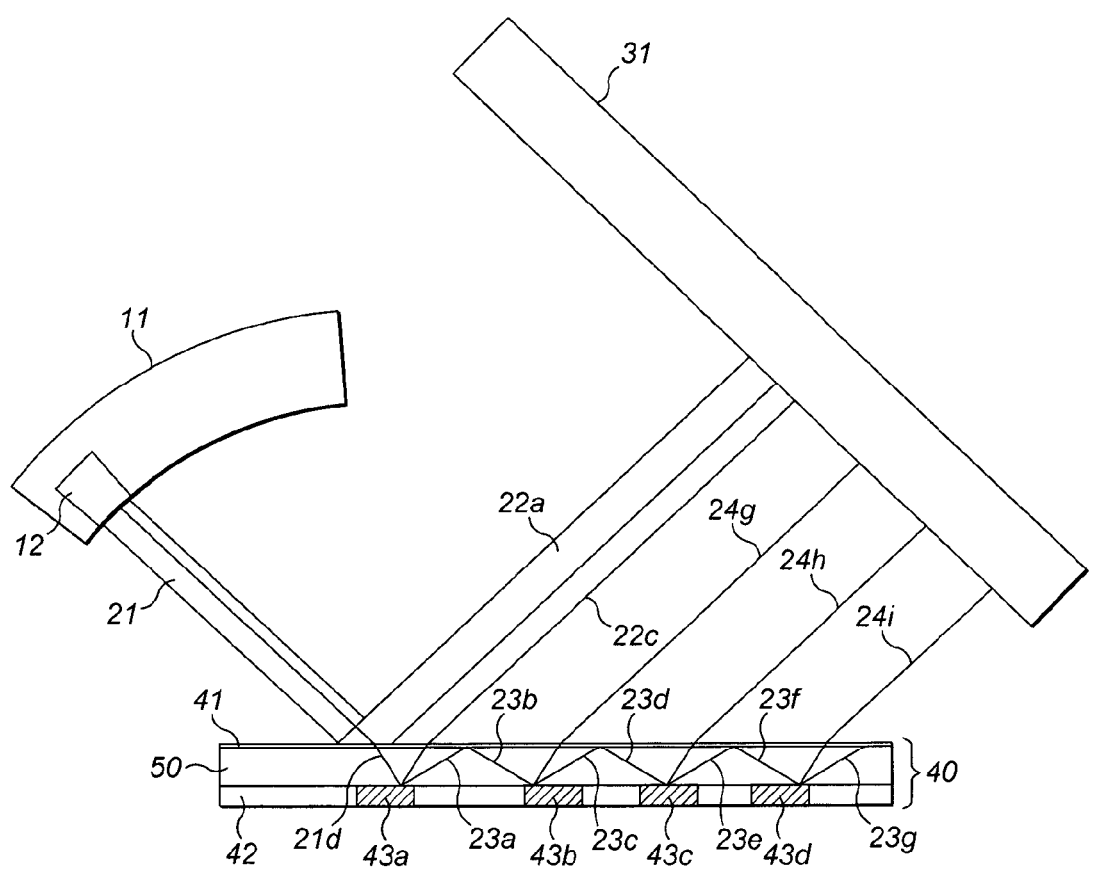

FIG. 5*d* illustrates the case wherein the third slit is opened in the photometric device previously illustrated in FIG. 4. Due to the particular light wavelength, incidence angle and particular position of the grating patterns, and due to the position o the open slit, four diffractive beams arrive into the detector (31), each corresponding to a different optical path. Following the same behavior illustrated in previous figures, the light beam is directed sequentially into each diffraction grating patterns (43*a*), (43*b*), (43*c*) and (43*d*), and each time a −1 reflective diffraction order exits the cartridge (40) and each time the zero diffractive order is first totally internal reflected in the upper surface (41) of the cartridge (40) before being diffracted in the next diffraction pattern.

In the embodiments illustrated in FIGS. 5*a* to 5*d*, the light intensity of each twice-diffracted optical path length is substantially the same, since only a second opposite diffraction occurs. This is achieved by selecting which slit to open as a function of the required path length/diffraction pattern at which the second diffraction should occur.

Some embodiments use narrow initial beams and cartridges with several opened slits. The narrow beams may be movable along an axis or are perpendicular to the beam path. In this way the choice of the total optical path length from specific discrete values can be made by moving the light emitter so that the beam enters the cartridge (40) in a corresponding slit. In some applications the total optical path must be sufficiently large to enable a good signal to noise ratio, while still being sufficiently small so it enables a proper measurement (e.g. without signal saturation, etc.). The example were detailed with a movable beam may then be used for a more general cartridge, and operated in the following way: (i) one or more light emitters are placed in a predefined positions along an axis of movement of the emitters; (ii) measurements are performed for a certain total optical path length corresponding to a specific entrance slit; (iii) internal quality control measurements are determined in terms of signal to noise ratio and/or signal saturation; (iv) results from internal quality control measurements are compared to pre-defined values established for acceptance/rejection criteria related to necessary total optical path length, and; (va) if acceptance criteria, in terms of total optical path length are reached, measurement values of the photometric data are further accepted and further processed, or (vb) if rejection criteria, in terms of total optical path length are reached, by confirming that the used optical path length is too small, then the emitter or emitters are moved to a new position corresponding to a larger optical path length and steps (ii) to (v) are again performed, or; (vc) if rejection criteria, in terms of total optical path length are reached, by confirming that the used optical path length is too large, then the emitter or emitters are moved to a new position corresponding to a smaller optical path length and steps (ii) to (v) are again performed.

In some alternative embodiments, the slits are simultaneously illuminated by a wide beam, resulting in a superposition of the light paths shown in FIGS. 5*b* to 5*d*. In these embodiments, rather than being selected by moving the emitter(s) (11), the appropriate path length is selected by selecting a corresponding one of the beams detected at the detector (31). The device and operation modes described above have significant advantages for analytical applications. In particular, the change of total optical path lengths in discrete steps, as opposed to continuous change, increases robustness and overall detection precision. Furthermore, the required optical path length may be directly related to the concentration of a compound to be detected. In complex samples the determination of multiple compounds having concentrations in substantially different ranges may be required. Known approaches require the adjustment of the sample dilution in different detection chambers in order to be able to fit the output signal within the detector device range. For high multiplex measurements this fact greatly increases device complexity. Exploiting the described embodiments, one may build and operate highly multiplexed detection devices with essentially the same dilutions for measuring compounds at significant different concentrations, by tuning the most appropriate optical path length for each compound.

In many applications one requires the use of movable cartridges, in particular centrifugal cartridges in which fluid flow is driven by rotating the cartridge, in order to perform multiplex measurements. Some embodiments provide a significant advantage for the photometric measurement in movable cartridges. In particular, the existence of multiple output beams, namely the first zero-order beam, and one or multiple −1 diffraction order beams (or other order beams) coming from the cartridge may be used to determine the position and orientation of the cartridge (40) with respect to the emitter (11) and/or with respect to the detector (31). By measuring not only the light intensities of the different diffracted beams from one or from multiple wavelengths, but also by measuring their relative distance, the position and/or orientation of the cartridge can be measured. This measurement may be used for quality control purposes, enabling in some cases the acceptance and/or rejection of certain measurements that show a cartridge position and/or orientation within or without a pre-defined acceptance/rejection range. In further more complex analytical systems, the position and/or orientation measurement may be used in an internal feedback loop for adjustment or correction of cartridge positions or orientations.

Figure 6:
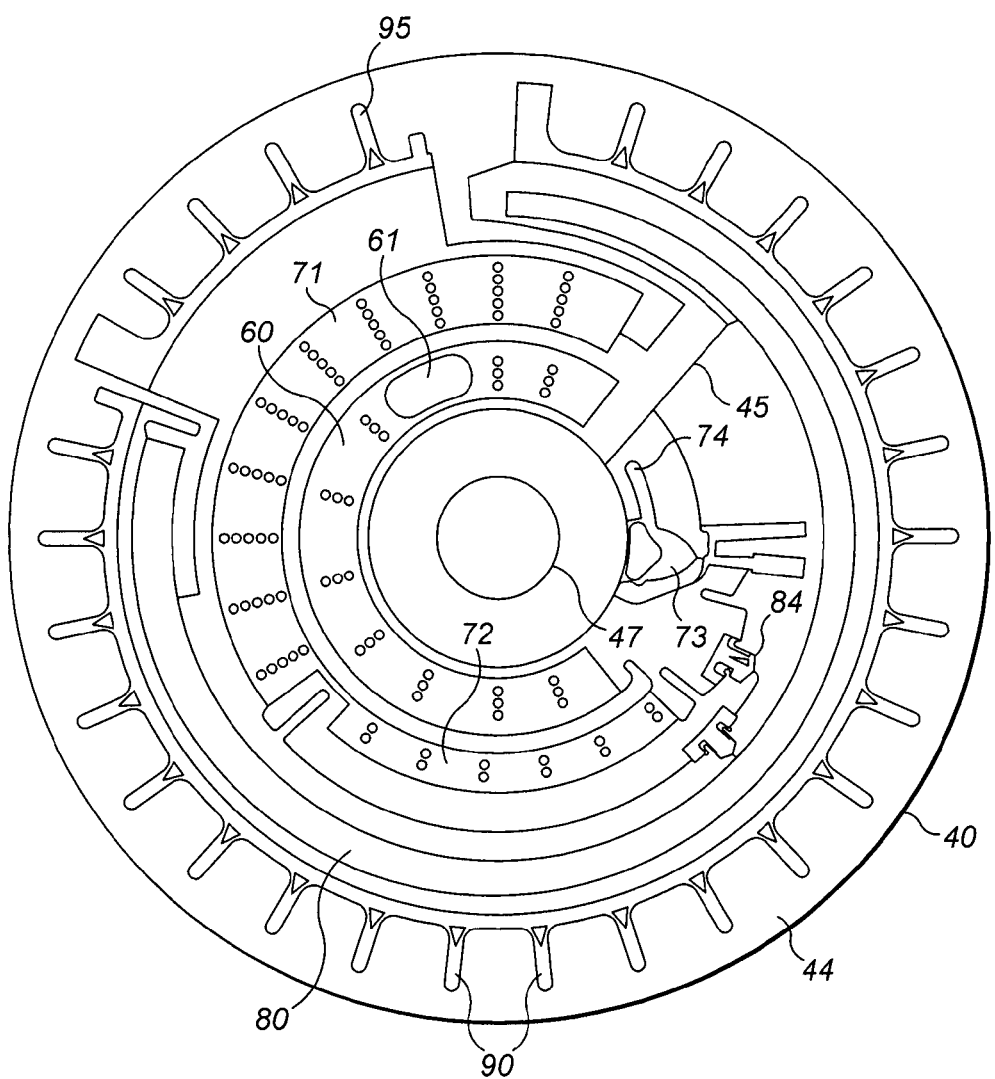
FIG. 6 illustrates a plane section of a centrifugal cartridge (40) incorporating photometric measurement chambers.

FIG. 6 illustrates a plan cross-sectional view of a centrifugal cartridge (40). The cartridge (40) contains different microfluidic structures for sample treatment and measurement of light adsorption at different detection areas. A initial reservoir (60) contains a liquid blister (61) with sufficient buffer for further processing. Blood is inserted in a blood inlet (74) and blood plasma with predefined volume is extracted in a specific blood plasma separation microfluidic structure (73). Buffer is aliquoted from the initial reservoir (60) into additional reservoirs with fixed volume (71) and (72) and blood plasma is diluted in a predefined ratio from the initial reservoirs into a dilution reservoir (80). From the dilution reservoir (80) liquid is routed into multiple detection zones (90) containing reagents that change light adsorption as a function of the presence and quantity of components on blood. The operation of the device enables detection of multiple blood parameters by simple action of rotation and by measuring the diffracted light passing through diluted blood plasma in the detection zones (90).

FIG. 7A illustrates a section view of the centrifugal cartridge illustrated in FIG. 6. The cartridge (40) consists of two disk parts (42) and (44) bonded together by a bonding layer (49). The upper disk (44) contains all fluidic structures previously illustrated in FIG. 6, and is operated in such a way to enable the determination of multiple blood parameters using simple rotation protocols, without additional external liquid pumps. The lower disk (42) contains grating patterns (43), used for providing light diffraction of multiple wavelengths, enabling in this way detection of different light beams passing through different optical path lengths of the diluted blood plasma. The cartridge (40) is of disk shape and contains one central hole (47) used for the coupling cartridge with a motor.

Figure 7B:
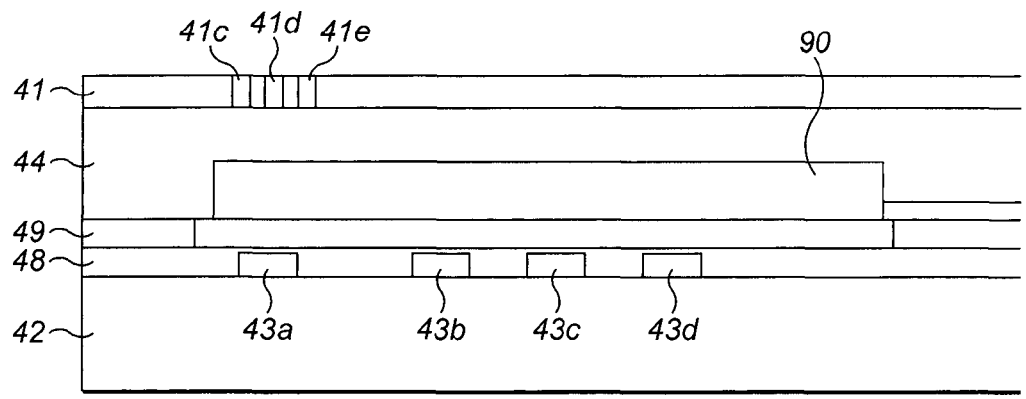
FIG. 7B illustrates details of the view in FIG. 7A.

FIG. 7B illustrates details of the device previously described with reference to FIG. 7A, showing multiple possible light entrance slits (41c), (41d) and (41e) and multiple grating pattern regions (43a), (43b), (43c) and (43d). The bonding layer (49) may be transparent or not, and may cut in the detection zones (90) in order to minimize light changes. The lower disk may contain a metal coating for reflection purposes on top of the grating regions.

Figure 8A:
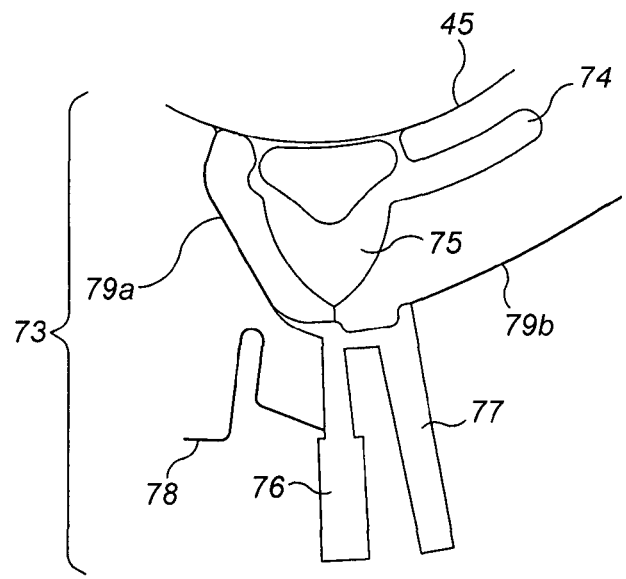
FIG. 8A illustrates a blood plasma extraction unit of the centrifugal cartridge in FIG. 6.

FIG. 8A illustrates a blood plasma extraction unit of the centrifugal cartridge. The blood is inserted in a blood inlet (74) and a predetermined blood volume is defined by the dimensions of a blood chamber (75). By rotating the cartridge (40) at a sufficiently high speed, blood moves from its initial position in the reservoir (75) into an outer reservoir (76) of smaller volume. This latter is connected to an overflow chamber (77) and to other structures by a plasma channel (78). Pressure balance of gas is maintained by air channels (45), (79a) and (79b). The volume defined by the connection between chambers (76) and (77) and the entrance of the channel (78) is the blood plasma volume extracted from the structure (73) and further used for measurement of blood parameters by photometric means according to the present invention.

Figure 8B:
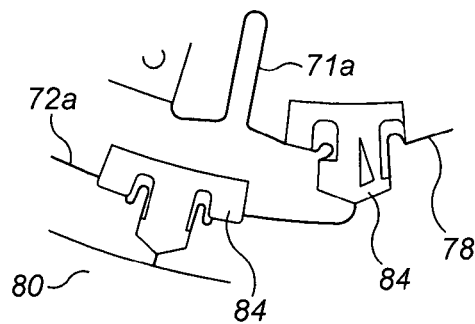
FIG. 8B illustrates a mixing unit of the centrifugal cartridge of FIG. 6.

FIG. 8B illustrates a mixing unit of the centrifugal cartridge, as described in International Application *PCT/PT*2009/000081, herewith incorporated by reference herein. A predefined blood plasma volume arrives from the channel (78) and is mixed in sequence in to mixing units (84) with buffer coming from different buffer chambers through channels (71a) and (72a). The mixed, diluted blood plasma is routed into a dilution chamber (80).

Figure 8C:
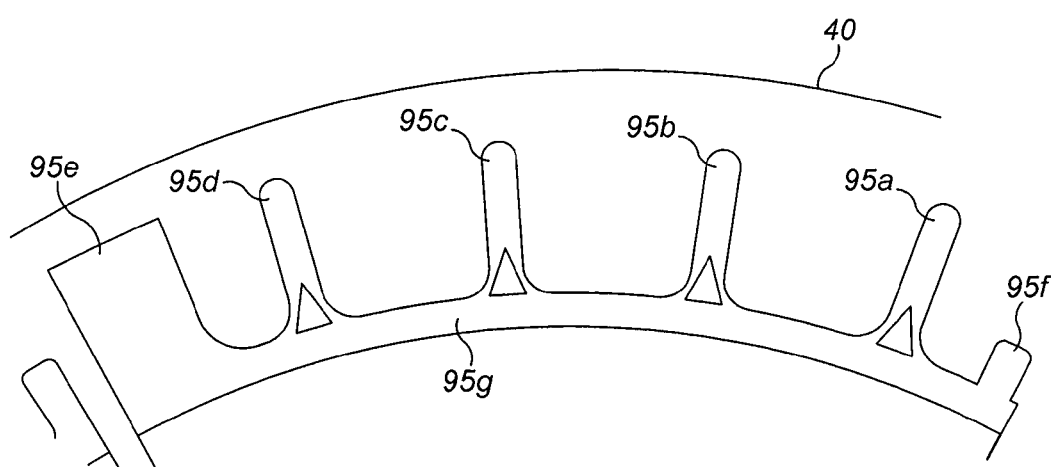
FIG. 8C illustrates several calibration detection units of the centrifugal cartridge of FIG. 6.

FIG. 8C illustrates several calibration detection units (95) of the centrifugal cartridge. The calibration detection units receive buffer and may contain reagents identical to the ones used in measurement detection zones (90). Buffer fills the distribution ring (95g) and all calibration detection units (95a), (95b), (95c) and (95d). Excess liquid is routed to the chamber (95e) so that precise volume is defined in each calibration detection zones.

Figure 8D:
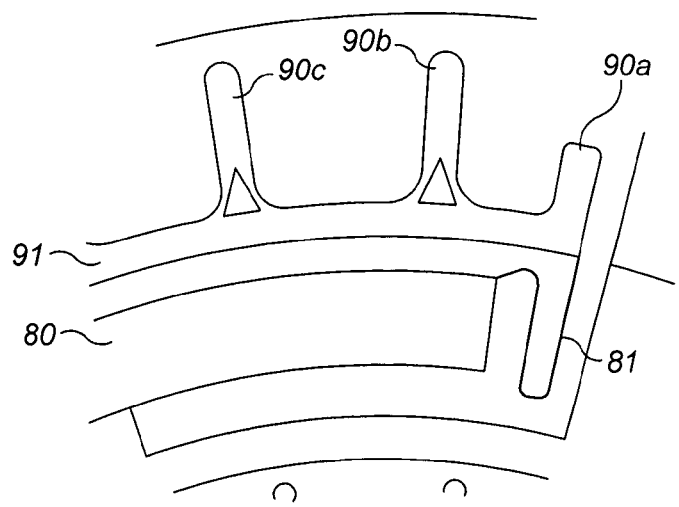
FIG. 8D illustrates several measurement detection units (90) of the centrifugal cartridge of FIG. 6.

FIG. 8D illustrates several measurement detection units (90) of the centrifugal cartridge. The diluted blood plasma is moved from the dilution chamber (80) into a distribution ring (91) using a distribution channel (81). Each detection unit (90b), (90c), etc may contain reagents responsible for the change of light properties, namely light absorption proportional to the concentration of corresponding blood plasma compounds.

Figure 8E:
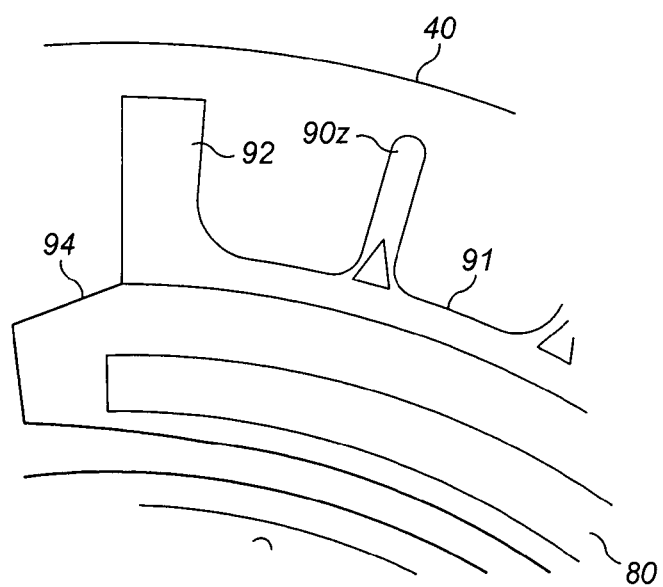
FIG. 8E illustrates measurement detection units (90) and an excess chamber (92) of the centrifugal cartridge of FIG. 6.

FIG. 8E illustrates measurement detection units (90) and an excess chamber (92) of the centrifugal cartridge. The distribution ring (91) enables the precise volume distribution of diluted blood plasma to each detection units (90a) to (90z) and excess liquid volume is routed to the excess chamber (92). Air pressure balance is maintained by means of an air channel (94).

In one embodiment, a device comprising a cartridge (40) illustrated in FIGS. 6, 7 and 8, and an emitter (11) and a detector (31) illustrated in previous figure (e.g. FIG. 2), may be operated as a total analytical system, performing in an automated manner, first microfluidic sample preparation tasks as illustrated above (e.g. blood plasma separation, blood plasma mixing and dilution) and then multiplexed light adsorption measurements at multiple wavelengths for the simultaneous determinations of different compounds present in blood.

A specific example of such an embodiment is now described. The analytical system includes a cartridge (40) as illustrated in FIGS. 6, 7 and 8, composed by two polycarbonate disk parts, each of 0.6 mm thickness, bonded together by a 0.02 mm bonding layer. One disk part (44) contains cavities in two depths of 0.2 mm and 0.05 mm, defining different chambers and channels. The other disk part (42) contains a grating structure on 800 nm period, 50 nm height and a 100 nm gold coating in some areas coincident with detection zone cavities of the upper disk part.

The cartridge includes a liquid blister having 80 uL of standard PBS buffer, sealed prior to use. Further to the plastic and bonding parts, the cartridge (40) includes dry reagents placed in the calibration detection zones and also in the measurement detection zones.

The system is operated in the following way:
(i) The liquid blister is rupture;
(ii) 15 μl of whole blood is inserted in the blood inlet
(iii) A predefined volume of 13 μl of whole blood fills the blood metering chamber by capillary action.
(iv) The cartridge is rotated at a sufficiently high rotational speed, and two events occur in parallel:
   a. The 13 μl of whole blood is moved into the blood plasma separation chamber and then exact blood metering of 12 μl if defined by having ~1 μl of blood overflowing the blood plasma chamber into the overflow chamber; and then the blood plasma is separated from blood cells by centrifugal action
   b. The standard buffer flows outwards from the blister chamber into aliquoting structures, defining a first volume of 15 μl in a first aliquot, 45 μl in a second aliquot, and then overflows the last 45 μl aliquot chamber into the calibration detection zones, wherein ~10 μl of buffer fill 4 calibration detection zones, and the excess of ~10 μlflows into the overflow chamber;
(v) After a sufficient long time to ensure proper blood plasma separation and proper buffer aliquoting, the cartridge is stopped, and the siphon 78 (as well as siphons retaining the buffer aliquots) is primed by capillary action;
(vi) the cartridge is again rotated at a 50 Hz and mixing is performed between first 15 μl of buffer and 3 μl of blood plasma and in sequence of 18 μl of diluted blood plasma with 45 μl buffer, moving a total of 63 μl of diluted blood plasma into the dilution chamber;
(vii) the cartridge is again stopped, and siphon at an outlet of the dilution chamber is primed by capillary action;
(viii) the cartridge is again rotated now at 25 Hz and the diluted blood plasma fills the detection chambers through a distribution chamber.
(ix) at the same time, while the cartridge is being rotated at a constant speed, light adsorption measurements are performed in both the calibration detection zones and in the measurement detection zones, at multiple wavelengths as described above, e.g. with reference to FIG. 2.
(x) light absorption at multiple wavelengths is measured and compared with calibration data to derive blood plasma concentration of different compounds.

The device built and operated according to the above description enables the simultaneous quantification of up to 21 blood parameters using only 15 μl of blood, in a DVD-like cartridge, with plastic parts produced with standard injection molding CD/DVD machinery. Furthermore, the cartridge may have identical detection zones and may be sufficiently flexible for different measurements, with different optical path lengths depending on the blood parameter to be measured. The implementation of a device according to the above provides significant advantages when compared to standard light adsorption systems, in several aspects:

The required total sample volume for highly multiplexed measurements is greatly reduced, by at least a factor of 6 (e.g. 90 uL of blood in other known systems compared to 15 uL of blood in the device described above). This fact may be of particular advantage for medical diagnostics, in particular point of care diagnostics;

The amount of reagents is also reduced by the same factor as the sample volume, leading to significant lower production costs of cartridges;

The cartridge required is of simple construction and may be manufactured at significantly lower costs;

The photometric measurements may be possible with internal quality controls and self-referencing, leading to higher signal to noise ratios and lowers risks of incorrect measurements, when compared to known systems.

The following is also disclosed:

A photometric measurement system comprising:
   a. A light source having at least one particular relevant wavelength,
   b. A detector,
   c. A cartridge for holding a liquid sample, compromising at least reflective grating surface,
wherein light is first diffracted inside the cartridge in a said first diffractive grating surface in contact with the liquid, in a certain diffraction order, then totally internal reflected in an different interface of the cartridge, and again diffracted in at least a said second diffractive surface in contact with the liquid, with the second diffraction occurring at an opposite sign diffraction order, and the second diffraction beam is detected by the optical detector, and photometric information of the relevant wavelength is extracted from the detected beam.

A system as described above, wherein the emitter consists of multiple wavelength sources, being LEDs or lasers or any other light source components. A system as described above, wherein the emitter consists of a light source with continuous spectrum and the detector contains multiple filters at specific wavelengths.

A system as described above, wherein the cartridge contains multiple optical entrance slits, and light incident in each slit is consecutively diffracted different number of times inside the cartridge, and the detector measures different spots each corresponding to different total optical paths inside the liquid.

A system as described above, wherein light adsorption measurements are performed for different wavelengths.

A system as described above, wherein the light emitter consists of a series of LEDs or Laser diodes with wavelengths of one or more of 340 nm, 405 nm, 467 nm, 500 nm, 550 nm, 600 nm, 630 nm, 780 nm and 850 nm.

A system as described above, wherein the detector consists of a 2-dimension optical detector, such as a CCD or CMOS image sensor.

A method to perform photometric measurements, wherein different wavelengths are incident to a cartridge containing liquid, having the cartridge multiple optical slits receiving the incident light beam, and the multiple beams are first diffracted inside the cartridge in a said first diffractive grating surface in contact with the liquid, in a certain diffraction order, then totally internal reflected in an different interface of the cartridge, and again diffracted in at least a said second diffractive surface in contact with the liquid, with the second diffraction occurring at an opposite sign diffraction order, and the second diffraction beam is detected by the optical detector, and photometric information is extracted from the detected beam.

A method as described above, wherein
   the relative distance between multiple diffracted beams of identical or of different wavelength are used to determine the cartridge relative position and relative orientation with respect to the emitter and/or to the detector;
   the position and light intensity of multiple diffracted beams is used for quality control purposes, with the measured distance between spots and/or intensity of multiple spots is compared to pre-defined values are measurements are accepted or rejected according to the results.

A method as described above, wherein
(i) the light intensity of multiple diffracted beams is used for measurement of photometric properties;
(ii) results are compared to pre-defined values are measurements are accepted or rejected according to the results;
(iii) if rejected the light emitter position is moved to a different position and light is incident to a different slit, and a the beam travels inside the liquid a different optical path; and steps (i) to (iii) are again performed.

A detection system as described above, wherein:
(i) the cartridge is of disk-shape, containing at least one blood inlet, a buffer blister, at least a mixing unit, and at least two detection zones;
(ii) specific reagents are placed in at least one detection zone, being capable of adsorbing light in the presence of some blood compounds, or being capable of enhancing some reaction that leads to light adsorption when in the presence of some blood plasma compound;
(iii) at least one of the surfaces contains a part with a reflective diffractive grating;
(iv) the cartridge is operated by rotation, performing in sequence, the blood plasma extraction, the blood plasma mixing and dilution;
(v) measurements are performed with ate least two wavelengths of beams having beam first diffracted then totally internal reflected and finally diffracted in an appositive sign diffraction;
(vi) light adsorption measurements are compared to calibration values;
(vii) concentrations in blood plasma are determined A detection system as described above, wherein blood is replaced by any other complex fluid containing compounds to be determined.

A production process of cartridges for photometric applications, comprising:
a. Bonding one plastic part having at least two cavities defining similar detection chambers to one plastic part having a diffraction grating in at least a fraction of its surface;
b. Creating different optical entrance slits on top of at least two cavities defining similar detection chambers, by means of paper or plastic label placement or by screen printing or any other printing method;
wherein each optical slit corresponds to a different total optical path for a photometric system using discrete multiple wavelengths.

It will be understood that the various embodiments described above can be combined as appropriate, and such combinations are included in this disclosure. For example, any of the described embodiments may be used in conjunction with centrifugal cartridges. Further, wavelength multiplexing as described with reference to FIGS. 2 and 3 can be combined with optical path length selection/multiplexing as described with reference to FIGS. 4 and 5a-d, for example by using several respective wide-beam light sources of the desired wavelengths.

The disclosure is not limited to any particular type of grating surfaces or patterns, and for each particular application the skilled person may choose specific grating shapes and profiles and patterns.

Furthermore, the disclosure is not limited to any specific type of cartridge dimensions or materials. In particular, the upper cartridge part (44) may be normally transparent to light or it may have patterns for reflection and transmission. Moreover, the disclosure is not limited to the use of light emitters comprising LEDs, since it may be implemented using lasers or diode lasers or any other suitable light source.

While described embodiments use reagents to affect light absorption as a function of target molecule concentration, some molecules, such as certain blood proteins, differentially absorb light at different frequencies, so that label free detection of such molecules without added reagents is included in the above description.

The disclosure is not limited to a microfluidic scale but applications on other, for example macroscopic scales are equally envisaged. For the avoidance of doubt, the term "microfluidic" is referred to herein to mean devices having a fluidic element such as a reservoir or a channel with at least one dimension below 1 mm.

The present invention is not intended to be limited to the particular described embodiments and examples but is defined by the appended claims.

The invention claimed is:

1. A method of deriving a photometric measure of a liquid disposed in a chamber between first and second chamber walls, the second chamber wall comprising one or more diffractive reflective surfaces, the method comprising:
directing a first light beam having a first wavelength through the first wall and liquid to a first location on the one or more diffractive reflective surfaces to cause the first light beam to be diffracted such that a first selected order beam of a first selected diffraction order is reflected at or in the first wall towards the second wall, the reflected first selected order beam being diffracted at a second location on the one or more diffractive reflective surfaces such that a first other order beam of a first other diffraction order, different from the first selected diffraction order, exits the chamber through the first wall;
detecting the first other order beam to derive a first signal relating to the first other order beam; and
deriving the photometric measure using the first signal.

2. A method as claimed in claim 1, wherein the first selected and other diffraction orders are diffraction orders of opposite sign.

3. A method as claimed in claim 1, wherein the first selected and other diffraction orders are first diffraction orders of opposite sign.

4. A method as claimed in claim 1, the method comprising detecting a beam reflected at the first location, deriving a normalisation signal related to the intensity of the beam reflected at the first location and using the normalisation signal to normalise an intensity of the first other order beam to derive the first signal.

5. A method as claimed in claim 1, the method comprising directing a second light beam having a second wavelength through the first wall to the first location to cause the second light beam to be diffracted such that a second selected order beam of a second selected diffraction order is reflected at or in the first wall towards the second wall, wherein the second selected order beam substantially coincides with the first selected order beam, the reflected second selected order beam being diffracted at a second location on the one or more diffractive reflective surfaces such that a second other order beam of a second other diffraction order, different from the second selected diffraction order, exits the chamber through the first wall, wherein the first and second selected diffraction orders are optionally the same and the first and second other diffraction orders are optionally the same;
detecting the second other order beam to derive a second signal relating to the second other order beam; and deriving the photometric measure using the first and second signal or deriving a second photometric measure using the second signal.

6. A method as claimed in claim 1, wherein the first selected order beam is reflected at least once at the second wall before being diffracted at the second location.

7. A method as claimed in claim 1, wherein the second wall comprises a plurality of diffractive reflective surfaces and a non-diffractive surface disposed between each pair of diffractive reflective surfaces, wherein the first selected order beam is reflected at least once at a non-diffractive surface at the second wall before being diffracted at the second location.

8. A method as claimed in claim 7, wherein the second location coincides with a first one of the plurality of diffractive reflective surfaces, the method comprising deriving a measure of signal quality of the first signal, determining whether the measure of signal quality meets a quality condition and, if the quality condition is not met: selecting a second one of the plurality of diffractive reflective surfaces, different from the first one, and changing the first location such that the second location coincides with the second one of the plurality of diffractive reflective surfaces.

9. A method as claimed in claim 8, wherein the first beam passes through an aperture in an opaque layer of the first wall and changing the first location includes moving the first beam to pass through a different aperture.

10. A method as claimed in claim 7, wherein a plurality of first locations are defined by corresponding apertures in an opaque layer of the first wall and the first beam illuminates the apertures to create a plurality of first beams such that corresponding second locations are each on a different one of the plurality of diffractive reflective surfaces, the method including detecting a resulting plurality of first other diffraction order beams.

11. A method as claimed in claim 1, the method comprising detecting a plurality of beams reflected from the second wall and using the plurality of beams to determine one or more of a position of the first location, a position of the second location and an orientation of the second wall.

12. A method as claimed in claim 1, wherein the liquid is a blood or blood serum sample.

13. A system comprising a light emitter, a light detector and a sample chamber, the light emitter, light detector and sample chamber being configured to enable derivation of a photometric measure using a method as claimed in claim 1.

14. A system as claimed in claim 13, the sample chamber being provided on a removable cartridge, and preferably wherein the system comprises a motor for rotating the cartridge to drive liquid flow in the cartridge.

15. The system of claim 13, wherein the sample chamber comprises a photometric measuring chamber.

16. A photometric measuring chamber for containing a liquid sample, the chamber comprising a first wall for transmitting an incident light beam and a second wall comprising a plurality of diffractive reflective surfaces and a respective non-diffractive reflective surface between each pair of diffractive reflective surfaces.

17. A photometric measuring chamber as claimed in claim 16, the first wall comprising an opaque layer in the region of a first one of the plurality of diffractive reflective surfaces, the opaque layer defining an aperture to allow a portion of the incident light beam to reach the first one of the plurality of diffractive surfaces.

18. A photometric measuring chamber as claimed in claim 17, the opaque layer defining a plurality of apertures.

19. A photometric measuring chamber as claimed in claim 16, the chamber being connected to a network of fluid conduits of a centrifugal microfluidic cartridge.

* * * * *